United States Patent
Kawasaki et al.

(10) Patent No.: US 10,987,764 B2
(45) Date of Patent: Apr. 27, 2021

(54) FLUX AND SOLDER PASTE

(71) Applicant: SENJU METAL INDUSTRY CO., LTD., Tokyo (JP)

(72) Inventors: Hiroyoshi Kawasaki, Tokyo (JP); Masato Shiratori, Tokyo (JP); Ko Inaba, Tokyo (JP); Hiroaki Kawamata, Tokyo (JP); Kazuhiro Minegishi, Tokyo (JP)

(73) Assignee: SENJU METAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/975,491

(22) PCT Filed: Oct. 11, 2018

(86) PCT No.: PCT/JP2018/037829
§ 371 (c)(1),
(2) Date: Aug. 25, 2020

(87) PCT Pub. No.: WO2019/167329
PCT Pub. Date: Sep. 6, 2019

(65) Prior Publication Data
US 2021/0031311 A1     Feb. 4, 2021

(30) Foreign Application Priority Data
Feb. 28, 2018  (JP) ............... JP2018-034440

(51) Int. Cl.
*B23K 35/00* (2006.01)
*B23K 35/362* (2006.01)
(Continued)

(52) U.S. Cl.
CPC .......... *B23K 35/362* (2013.01); *B23K 35/025* (2013.01); *B23K 35/24* (2013.01); *B23K 2103/30* (2018.08)

(58) Field of Classification Search
CPC ... C08L 93/04; B23K 35/262; B23K 2101/42; B23K 35/0244; B23K 35/025;
(Continued)

(56) References Cited

U.S. PATENT DOCUMENTS

| | | | |
|---|---|---|---|
| 5,584,942 A | 12/1996 | Satsurai | |
| 2013/0299219 A1* | 11/2013 | Chisaka | H05K 1/185 174/257 |

(Continued)

FOREIGN PATENT DOCUMENTS

| | | |
|---|---|---|
| JP | H01150493 A | 6/1989 |
| JP | H0639585 A | 2/1994 |

(Continued)

OTHER PUBLICATIONS

International Search Report of the International Searching Authority (in English and Japanese) issued in PCT/JP2018/037829, dated Dec. 25, 2018; ISA/JP.

*Primary Examiner* — Erin B Saad
(74) *Attorney, Agent, or Firm* — Harness, Dickey & Pierce, P.L.C.

(57) ABSTRACT

It is an object of the present invention to provide a flux containing flux components homogeneously dispersed without precipitation of aggregates in addition to having an appropriate balance between fluidity and shape retention property, and a solder paste. A flux comprising 0.5 to 3.5 mass % of a sorbitol-type thixotropic agent selected from the group consisting of dibenzylidene sorbitol, bis(4-methylbenzylidene)sorbitol and a combination thereof, and 2 to 350 mass ppm of a sorbitol-type additive selected from the group consisting of sorbitol, monobenzylidene sorbitol, mono(4-methylbenzylidene)sorbitol and a combination thereof, and a glycol ether-type solvent.

16 Claims, 1 Drawing Sheet

(51) Int. Cl.
*B23K 35/24* (2006.01)
*B23K 35/02* (2006.01)
*B23K 103/00* (2006.01)

(58) Field of Classification Search
CPC .... B23K 35/24; B23K 35/302; B23K 35/362; B23K 1/00; B23K 1/0016; B23K 1/19; B23K 1/20; B23K 2101/34; B23K 2101/36; B23K 2103/12; B23K 35/0233; B23K 35/22; B23K 35/26; B23K 35/3615; B23K 35/38; B23K 37/003; B23K 3/04; B23K 3/0638
USPC .......................................................... 148/23
See application file for complete search history.

(56) References Cited

U.S. PATENT DOCUMENTS

| | | | |
|---|---|---|---|
| 2013/0343023 A1* | 12/2013 | Nakagoshi | H05K 3/368 |
| | | | 361/767 |
| 2014/0178703 A1* | 6/2014 | Nakano | B23K 35/025 |
| | | | 428/457 |
| 2019/0009375 A1* | 1/2019 | Hayashi | C22C 13/00 |
| 2019/0015937 A1* | 1/2019 | Nakaji | C08K 5/092 |

FOREIGN PATENT DOCUMENTS

| | | |
|---|---|---|
| JP | H06335794 A | 12/1994 |
| JP | 201077271 A | 4/2010 |
| JP | 201649567 A | 4/2016 |
| JP | 6027655 B2 | 10/2016 |
| JP | 201730039 A | 2/2017 |

\* cited by examiner

FLUX AND SOLDER PASTE

CROSS REFERENCE TO RELATED APPLICATIONS

This application is a U.S. National Phase Application under 35 U.S.C. 371 of International Application No. PCT/JP2018/037829 filed on Oct. 11, 2018, which claims the benefit of priority from Japanese Patent Application No. 2018-034440 filed Feb. 28, 2018. The entire disclosures of all of the above applications are incorporated herein by reference.

TECHNICAL FIELD

The present invention relates to a flux and a solder paste.

BACKGROUND ART

Fixing and electrical connection of electronic parts in electronic equipment, such as mounting of electronic parts on a printed circuit board, is generally carried out by soldering, which is most advantageous in terms of cost and reliability. Methods generally adopted for this kind of soldering include a flow soldering method in which a printed circuit board and an electronic part are brought into contact with molten solder to carry out soldering, and a reflow soldering method in which solder in the form of a solder paste, a solder preform or a solder ball is remelted in a reflow furnace to carry out soldering.

The solder paste used in this reflow soldering method is a mixture obtained by kneading a solder powder and a flux that is a component other than the solder powder, including a rosin-type resin, an activator, a thixotropic agent or a solvent, into a paste.

Since feeding of a solder paste to a board is usually carried out by dispenser discharging or screen printing, the solder paste is required to have dischargeability and printability such as release property, and is further required to retain its shape after it is fed. In a solder paste, flow characteristics (thixotropy) including both of fluidity (low viscosity) during discharging/printing and shape retention property (high viscosity) after feeding become an important factor during fine pitch printing in the board surface mounting in which an increase in density has been accelerated in recent years.

In order to impart thixotropy, a thixotropic agent is added to a flux used in a solder paste.

As the thixotropic agent, a sorbitol-type thixotropic agent such as dibenzylidene sorbitol or bis(4-methylbenzylidene) sorbitol is known. For example, in Patent Literature 1, a soldering flux containing a combination of a prescribed amount of hydrogenated castor oil and dibenzylidene sorbitol or dimethyldibenzylidene sorbitol is proposed.

However, it has been found that coarse aggregates exist in the flux containing a combination of hydrogenated castor oil and dibenzylidene sorbitol, as described later in a comparative example of the present application. If coarse aggregates are contained in a flux during soldering, the aggregates physically hinder the formation of an alloy layer of an electrode and solder and cause occurrence of non-wetting. Moreover, existence of these aggregates hinders homogeneity of flux components, and if the flux components become heterogeneous, solder wettability becomes heterogeneous.

As described above, a flux containing flux components homogeneously dispersed without precipitation of aggregates in addition to having an appropriate balance between fluidity and shape retention property is desired.

CITATION LIST

Patent Literature

PTL 1: Japanese Patent No. 6027655

SUMMARY OF INVENTION

Technical Problem

It is an object of the present invention to provide a flux containing flux components homogeneously dispersed without precipitation of aggregates in addition to having an appropriate balance between fluidity and shape retention property, and a solder paste.

Solution to Problem

In order to solve the above problem, the present inventors have earnestly studied, and as a result, they have found that the above problem can be solved by using a flux containing a specific amount of a sorbitol-type thixotropic agent, a specific amount of a sorbitol-type additive and a glycol ether-type solvent, and have completed the present invention. Specific aspects of the present invention are as follows.

Herein, when a numerical value range is indicated by using "to", the range includes numerical values of the both ends.

[1] A flux comprising: 0.5 to 3.5 mass % of a sorbitol-type thixotropic agent selected from the group consisting of dibenzylidene sorbitol, bis(4-methylbenzylidene)sorbitol and a combination thereof; 2 to 350 mass ppm of a sorbitol-type additive selected from the group consisting of sorbitol, monobenzylidene sorbitol, mono(4-methylbenzylidene)sorbitol and a combination thereof; and a glycol ether-type solvent.

[2] The flux according to [1], wherein a content of the sorbitol-type additive is 0.05 to 1.00 mass % based on the total amount of the sorbitol-type thixotropic agent and the sorbitol-type additive.

[3] The flux according to [1] or [2], further comprising 1.0 to 10.0 mass % of a thixotropic agent other than the sorbitol-type thixotropic agent.

[4] The flux according to any one of [1] to [3], further comprising 20.0 to 60.0 mass % of a rosin-type resin and/or a water-soluble resin, 0 to 10.0 mass % of an organic acid, 0 to 5.0 mass % of an amine compound, 0 to 5.0 mass % of an organohalogen compound, 0 to 3.0 mass % of an amine hydrohalide salt, and 0 to 5.0 mass % of an antioxidant.

[5] A solder paste comprising the flux according to any one of [1] to [4] and a solder powder.

Advantageous Effects of Invention

The flux of the present invention contains flux components homogeneously dispersed without precipitation of aggregates, in addition to having an appropriate balance between fluidity and shape retention property.

The present inventors have found that when the content of a sorbitol-type thixotropic agent such as dibenzylidene sorbitol or bis(4-methylbenzylidene)sorbitol is increased, aggregates are precipitated. Then, they have found that when the content of a sorbitol-type thixotropic agent is increased, precipitation of aggregates can be suppressed by using a specific amount of a sorbitol-type additive and a glycol ether-type solvent. Details of the reason for this are not clear, but they are presumed to be as follows.

A low-molecular type thixotropic agent is associated owing to a noncovalent bonding interaction such as hydrogen bonding or $\pi$-$\pi$ stacking, and forms an associated body such as a needle crystal. In addition, in a composition such as a flux or a solder paste, an interaction takes place among the associated bodies of the thixotropic agent to form a network of three-dimensional network structure, and owing to this network formation, thixotropy is imparted.

In the low-molecular type thixotropic agent, a needle crystal is formed prior to formation of a network of three-dimensional network structure, as described above; however it is thought that because the sorbitol-type thixotropic agent has high crystallizability, crystals are liable to be precipitated, and that those crystals are further aggregated to easily form coarse aggregates. Then, it is thought that by adding a sorbitol-type additive having a molecule of analogous structure in order to suppress excessive precipitation of crystals of the sorbitol-type thixotropic agent and suppress formation of coarse aggregates, the sorbitol-type additive is appropriately incorporated into a molecular assembly of the sorbitol-type thixotropic agent, whereby crystallizability can be reduced and formation of coarse aggregates can be suppressed.

DESCRIPTION OF EMBODIMENTS

Figure 1:
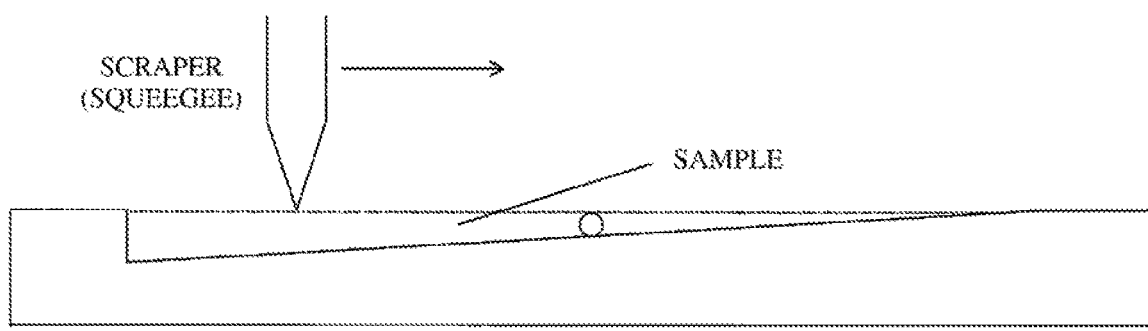
FIG. 1 is a sectional view showing a state of measurement of a sample using a grindometer.

The flux and the solder paste of the present invention will be described hereinafter.

The flux of the present invention comprises a sorbitol-type thixotropic agent selected from the group consisting of dibenzylidene sorbitol, bis(4-methylbenzylidene)sorbitol and a combination thereof, and a sorbitol-type additive selected from the group consisting of sorbitol, monobenzylidene sorbitol, mono(4-methylbenzylidene)sorbitol and a combination thereof, and a glycol ether-type solvent.

The content of the sorbitol-type thixotropic agent is 0.5 to 3.5 mass %, preferably 0.5 to 2.5 mass %, more preferably 0.5 to 1.5 mass % based on the mass of the whole flux.

The content of the sorbitol-type additive is 2 to 350 ppm (0.0002 to 0.0350 mass %), preferably 7 to 250 ppm (0.0007 to 0.0250 mass %), more preferably 10 to 150 ppm (0.0010 to 0.0150 mass %) based on the mass of the whole flux.

The content of the sorbitol-type additive is preferably 0.05 to 1.00 mass %, more preferably 0.05 to 0.50 mass %, most preferably 0.10 to 0.30 mass % based on the total amount of the sorbitol-type thixotropic agent and the sorbitol-type additive. When the content of the sorbitol-type additive is in the above range based on the total amount of the sorbitol-type thixotropic agent and the sorbitol-type additive, precipitation of coarse aggregates can be suppressed.

As the glycol ether-type solvent, an aliphatic glycol ether-type solvent, such as hexyl glycol, hexyl diglycol, 2-ethylhexyl glycol, 2-ethylhexyl diglycol, dimethyl triglycol, dibutyl diglycol or tetraethylene glycol dimethyl ether, or an aromatic glycol ether-type solvent, such as phenyl glycol, phenyl diglycol, benzyl glycol or benzyl diglycol, can be used, and the aromatic glycol ether-type solvent has a higher effect of suppressing precipitation of aggregates.

When the sorbitol-type thixotropic agent and the sorbitol-type additive are used in the above ranges of the contents in combination with the glycol ether-type solvent, a balance between fluidity and shape retention property can be kept while precipitation of aggregates is suppressed.

The flux of the present invention can further contain a thixotropic agent other than the sorbitol-type thixotropic agent.

As the thixotropic agent other than the sorbitol-type thixotropic agent, an amide-type thixotropic agent, an ester-type thixotropic agent, or the like can be used.

As the amide-type thixotropic agent, fatty acid monoamide, fatty acid bisamide, fatty acid alkanolamide, aromatic amide, polyamide, or the like can be used. Examples of the fatty acid monoamides include higher fatty acid amides such as stearic acid amide. Examples of the fatty acid bisamides include ethylenebisstearic acid amide, ethylenebishydroxystearic acid amide, hexamethylenehydroxystearic acid amide, and methylenebisstearic acid amide. Examples of the fatty acid alkanolamides include palmitic acid monoethanolamide. Examples of the aromatic amides include 4-methylbenzamide. Examples of the ester-type thixotropic agents include hydrogenated castor oil and hydrogenated castor oil derivatives. Of these, hydrogenated castor oil is preferable in view of stability with time, and an amide-type thixotropic agent, particularly bisamide or polyamide, is preferable in view of suppression of heat sagging.

As the thixotropic agent other than the sorbitol-type thixotropic agent, the above compounds can be used singly or in combination of two or more.

The content of the thixotropic agent other than the sorbitol-type thixotropic agent is preferably 1.0 to 10.0 mass %, more preferably 2.0 to 10.0 mass %, most preferably 3.0 to 8.0 mass % based on the mass of the whole flux. When the content of the thixotropic agent other than the sorbitol-type thixotropic agent is in the above range, there is provided the effect of suppressing precipitation of aggregates and also imparting higher thixotropy than in the case where the sorbitol-type thixotropic agent is used singly.

The flux of the present invention can further contain 20.0 to 60.0 mass % of a rosin-type resin and/or a water-soluble resin, 0 to 10.0 mass % of an organic acid, 0 to 5.0 mass % of an amine compound, 0 to 5.0 mass % of an organohalogen compound, 0 to 3.0 mass % of an amine hydrohalide salt, and 0 to 5.0 mass % of an antioxidant.

Examples of the rosin-type resins include raw material rosins, such as gum rosin, wood rosin and tall oil rosin, and derivatives obtained from the raw material rosins. Examples of the derivatives include purified rosin, hydrogenated rosin, disproportionated rosin, polymerized rosin, an $\alpha,\beta$-unsaturated carboxylic acid modified product (acrylated rosin, maleated rosin, fumerated rosin or the like), and a purified product, a hydrogenated product and a disproportionated product of the polymerized rosin, and a purified product, a hydrogenated product and a disproportionated product of the $\alpha,\beta$-unsaturated carboxylic acid modified product, and these can be used in combination of two or more.

The content of the rosin-type resin is 20.0 to 60.0 mass %, preferably 30.0 to 60.0 mass %, more preferably 40.0 to 60.0 mass % based on the mass of the whole flux. When the content of the rosin-type resin is in the above range, a flux having an appropriate viscosity can be formed, and the flux exhibits good solder wettability during reflowing.

In addition to the rosin-type resin, at least one other resins selected from an acrylic resin, an acrylic-polyethylene resin, an acrylic-vinyl acetate resin, a polyethylene resin, a polypropylene resin, a polyethylene polypropylene resin, a terpene resin, a modified terpene resin, a terpene phenol resin, a modified terpene phenol resin, a styrene resin, a modified styrene resin, a xylene resin and a modified xylene resin can be further contained. As the modified terpene resin, an aromatic modified terpene resin, a hydrogenated terpene resin, a hydrogenated aromatic modified terpene resin, or the like can be used. As the modified terpene phenol resin, a hydrogenated terpene phenol resin, or the like can be used. As the modified styrene resin, a styrene acrylic resin, a styrene-maleic acid resin, or the like can be used. As the modified xylene resin, a phenol-modified xylene resin, an alkylphenol-modified xylene resin, a phenol-modified resol type xylene resin, a polyol-modified xylene resin, a polyoxyethylene-added xylene resin, or the like can be used.

The total content of the above other resins is preferably 0 to 60.0 mass %, more preferably 5.0 to 50.0 mass %, most preferably 10.0 to 40.0 mass % based on the mass of the whole flux.

As the water-soluble resin, at least one selected from polyethylene glycol, EO, PO or EO/PO ester adducts of various alcohols, and EO, PO or EO/PO amide adducts of various amines can be used.

The total content of the water-soluble resins is 20.0 to 60.0 mass %, preferably 30.0 to 60.0 mass %, more preferably 40.0 to 60.0 mass % based on the mass of the whole flux.

As the organic acid, glutaric acid, succinic acid, maleic acid, adipic acid, DL-malic acid, diglycolic acid, azelaic acid, eicosanedioic acid, citric acid, glycolic acid, salicylic acid, dipicolinic acid, dibutylaniline diglycolic acid, suberic acid, sebacic acid, thioglycolic acid, terephthalic acid, dodecanedioic acid, para-hydroxyphenylacetic acid, picolinic acid, phenylsuccinic acid, phthalic acid, fumaric acid, malonic acid, lauric acid, benzoic acid, tartaric acid, tris(2-carboxyethyl)isocyanurate, glycine, 1,3-cyclohexanedicarboxylic acid, 2,2-bis(hydroxymethyl)propionic acid, 2,2-bis(hydroxymethyl)butanoic acid, 2,3-dihydroxybenzoic acid, 2,4-diethylglutaric acid, 2-quinolinecarboxylic acid, 3-hydroxybenzoic acid, p-anisic acid, stearic acid, 12-hydroxystearic acid, oleic acid, linoleic acid, linolenic acid, dimer acid, hydrogenated dimer acid, trimer acid, hydrogenated trimer acid, or the like can be used, and in view of good solder wettability, it is preferable to use glutaric acid, adipic acid, azelaic acid, sebacic acid, dimer acid, hydrogenated dimer acid, trimer acid or hydrogenated trimer acid.

The content of the organic acid is 0 to 10.0 mass %, preferably 2.0 to 10.0 mass %, more preferably 4.0 to 10.0 mass % based on the mass of the whole flux. When the content of the organic acid is in the above range, good solder wettability is exhibited.

As the amine compound, aliphatic amine, aromatic amine, amino alcohol, imidazole, benzotriazole, amino acid, guanidine, hydrazide, or the like can be used. Examples of the aliphatic amines include dimethylamine, ethylamine, 1-aminopropane, isopropylamine, trimethylamine, allylamine, n-butylamine, diethylamine, sec-butylamine, tert-butylamine, N,N-dimethylethylamine, isobutylamine, and cyclohexylamine. Examples of the aromatic amines include aniline, N-methylaniline, diphenylamine, N-isopropylaniline, and p-isopropylaniline. Examples of the amino alcohols include 2-aminoethanol, 2-(ethylamino)ethanol, diethanolamine, diisopropanolamine, triethanolamine, N-butyldiethanolamine, triisopropanolamine, N,N-bis(2-hydroxyethyl)-N-cyclohexylamine, N,N,N',N'-tetrakis(2-hydroxypropyl) ethylenediamine, and N,N,N',N'',N''-pentakis(2-hydroxypropyl)diethylenetriamine. Examples of the imidazoles include 2-methylimidazole, 2-undecylimidazole, 2-heptadecylimidazole, 1,2-dimethylimidazole, 2-ethyl-4-methylimidazole, 2-phenylimidazole, 2-phenyl-4-methylimidazole, 1-benzyl-2-methylimidazole, 1-benzyl-2-phenylimidazole, 1-cyanoethyl-2-methylimidazole, 1-cycanoethyl-2-undecylimidazole, 1-cyanoethyl-2-ethyl-4-methylimidazole, 1-cyanoethyl-2-phenylimidazole, 1-cyanoethyl-2-undecylimidazolium trimellitate, 1-cyanoethyl-2-phenylimidazolium trimellitate, 2,4-diamino-6-[2'-methylimidazolyl-(1')]-ethyl-s-triazine, 2,4-diamino-6-[2'-undecylimidazolyl-(1')]-ethyl-s-triazine, 2,4-diamino-6-[2'-ethyl-4'-methylimidazolyl-(1')]-ethyl-s-triazine, 2,4-diamino-6-[2'-methylimidazolyl-(1')]-ethyl-s-triazine isocyanuric acid adduct, 2-phenylimidazole isocyanuric acid adduct, 2-phenyl-4,5-dihydroxymethylimidazole, 2-phenyl-4-methyl-5-hydroxymethylimidazole, 2,3-dihydro-1H-pyrrolo[1,2-a]benzimidazole, 2-methylimidazoline, 2-phenylimidazoline, 2,4-diamino-6-vinyl-s-triazine, 2,4-diamino-6-vinyl-s-triazine isocyanuric acid adduct, 2,4-diamino-6-methacryloyloxyethyl-s-triazine, epoxy-imidazole adduct, 2-methylbenzimidazole, 2-octylbenzimidazole, 2-pentylbenzimidazole, 2-(1-ethylpentyl)benzimidazole, 2-nonylbenzimidazole, 2-(4-thizolyl)benzimidazole, and benzimidazole. Examples of the benzotriazoles include 2-(2'-hydroxy-5'-methylphenyl)benzotriazole, 2-(2'-hydroxy-3',5'-di-tert-amylphenyl)benzotriazole, 2-(2'-hydroxy-5'-tert-octylphenyl)benzotriazole, 2,2'-methylenebis[6-(2H-benzotriazol-2-yl)-4-tert-octylphenol], 6-(2-benzotriazolyl)-4-tert-octyl-6'-tert-butyl-4'-methyl-2,2'-methylenebisphenol, 1,2,3-benzotriazole, 1-[N,N-bis(2-ethylhexyl)aminomethyl] benzotriazole, carboxybenzotriazole, 1-[N,N-bis(2-ethylhexyl)aminomethyl]methylbenzotriazole, 2,2'-[[methyl-1H-benzotriazol-1-yl)methyl]imino]bisethanol, 1,2,3-benzotriazole sodium salt aqueous solution, 1-(1',2'-dicarboxyethyl)benzotriazole, 1-(2,3-dicarboxypropyl)benzotriazole, 1-[(2-ethylhexylamino)methyl]benzotriazole, 2,6-bis[(1H-benzotriazol-1-yl)methyl]-4-methylphenol, and 5-methylbenzotriazole. Examples of the amino acids include alanine, arginine, asparagine, aspartic acid, glutamine, glutamic acid, glycine, histidine, isoleucine, leucine, methionine, phenylalanine, proline, serine, threonine, tryptophan, tyrosine, valine, β-alanine, γ-aminolactic acid, δ-aminovaleric acid, ε-aminohexanoic acid, ε-caprolactam, and 7-aminoheptanoic acid. Examples of the guanidines include dicyandiamide, 1,3-diphenylguanidine, and 1,3-di-o-tolylguanidine. Examples of the hydrazides include carbodihydrazide, malonic acid dihydrazide, succinic acid dihydrazide, adipic acid dihydrazide, 1,3-bis(hydrazinocarbonoethyl)-5-isopropyl hydantoin, sebacic acid dihydrazide, dodecanedioic acid dihydrazide, 7,11-octadecadiene-1,18-dicarbohydrazide, and isophthalic acid dihydrazide. Of these, imidazoles and aromatic guanidines are preferable in view of good solderability.

The content of the amine compound is 0 to 5.0 mass %, preferably 2.0 to 5.0 mass % based on the mass of the whole flux. When the content of the amine compound is in the above range, good solderability is exhibited.

As the organohalogen compound, trans-2,3-dibromo-2-butene-1,4-diol, 2,3-dibromo-1,4-butanediol, 2,3-dibromo-1-propanol, 2,3-dichloro-1-propanol, 1,1,2,2-tetrabromoethane, 2,2,2-tribromoethanol, pentabromoethane, carbon tetrabromide, 2,2-bis(bromomethyl)-1,3-propanediol, meso-2,3-dibromosuccinic acid, chloroalkane, chlorinated fatty acid ester, n-hexadecyltrimethylammonium bromide, triallyl isocyanurate hexabromide, 2,2-bis[3,5-dibromo-4-(2,3-dibromopropoxy)phenyl]propane, bis[3,5-dibromo-4-(2,3-dibromopropoxy)phenyl]sulfone, ethylenebispentabromobenzene, 2-chloromethyloxylan, HET acid, HET anhydride, brominated bisphenol A type epoxy resin, or the like can be used, and in view of good solderability, trans-2,3-dibromo-2-butene-1,4-diol, meso-2,3-dibromosuccinic acid, or triallyl isocyanurate hexabromide is preferable.

The content of the organohalogen compound is preferably 0 to 5.0 mass %, more preferably 0 to 3.0 mass % based on the mass of the whole flux. When the content of the organohalogen compound is in the above range, good solderability is exhibited.

As the amine hydrohalide salt, a hydrohalide salt of the aforesaid amine compound (salt of HF, HCl, HBr or HI) can be used. Examples of the amine hydrohalide salts include stearylamine hydrochloride, diethylaniline hydrochloride, diethanolamine hydrochloride, 2-ehylhexylamine hydrobromide, pyridine hydrobromide, isopropylamine hydrobromide, cyclohexylamine hydrobromide, diethylamine hydrobromide, monoethylamine hydrobromide, 1,3-diphenylguanidine hydrobromide, dimethylamine hydrobromide, dimethylamine hydrochloride, rosin amine hydrobromide, 2-ethylhexylamine hydrochloride, isopropylamine hydrochloride, cyclohexylamine hydrochloride, 2-pipecoline hydrobromide, 1,3-diphenylguanidine hydrochloride, dimethylbenzylamine hydrochloride, hydrazine hydrate hydrobromide, dimethylcyclohexylamine hydrochloride, trinonylamine hydrobromide, diethylaniline hydrobromide, 2-diethylaminoethanol hydrobromide, 2-diethylaminoethanol hydrochloride, ammonium chloride, diallylamine hydrochloride, diallylamine hydrobromide, monoethylamine hydrochloride, monoethylamine hydrobromide, diethylamine hydrochloride, triethylamine hydrobromide, triethylamine hydrochloride, hydrazine monohydrochloride, hydrazine dihydrochloride, hydrazine monohydrobromide, hydrazine dihydrobromide, pyridine hydrochloride, aniline hydrobromide, butylamine hydrochloride, hexylamine hydrochloride, n-octylamine hydrochloride, dodecylamine hydrochloride, dimethylcyclohexylamine hydrobromide, ethylenediamine dihydrobromide, rosin amine hydrobromide, 2-phenylimidazole hydrobromide, 4-benzylpyridine hydrobromide, L-glutamic acid hydrochloride, N-methylmorpholine hydrochloride, betaine hydrochloride, 2-pipecoline hydroiodide, cyclohexylamine hydroiodide, 1,3-diphenylguanidine hydrofluoride, diethylamine hydrofluoride, 2-ethylhexylamine hydrofluoride, cyclohexylamine hydrofluoride, ethylamine hydrofluoride, and rosin amine hydrofluoride, and in view of good solderability and electrical reliability, amine hydrobromide salt is preferable.

The content of the amine hydrohalide salt is 0 to 3.0 mass %, preferably 0 to 1.0 mass % based on the mass of the whole flux. When the content of the amine hydrohalide salt is in the above range, good solderability and electrical reliability are exhibited.

As the antioxidant, a hindered phenol-type antioxidant such as 2,2'-methylenebis[6-(1-methylcyclohexyl)-p-cresol] can be used. The content of the antioxidant based on the mass of the whole flux is 0 to 5.0 mass %.

The flux of the present invention can further contain amine borohydrofluoride salt.

As the amine borohydrofluoride salt, a borohydrofluoride salt of the aforesaid amine compound can be used. Examples of the amine borohydrofluoride salts include cyclohexylamine tetrafluoroborate and dicyclohexylamine tetrafluoroborate.

The content of the amine borohydrofluoride salt is preferably 0 to 1.0 mass % based on the mass of the whole flux. When the content of the amine borohydrofluoride salt is in the above range, good solderability is exhibited.

The solder paste of the present invention comprises the aforesaid flux and a solder powder.

The "flux" in the solder paste of the present invention refers to the whole of components other than the solder powder in the solder paste. In the solder paste of the present invention, the weight ratio between the solder powder and the flux (solder powder:flux) can be appropriately set according to the use purpose.

As alloy compositions of the solder paste, an Sn—Ag based alloy, an Sn—Cu based alloy, an Sn—Ag—Cu based alloy, an Sn—In based alloy, an Sn—Bi based alloy, an Sn—Sb based alloy, and alloys in which Ag, Cu, Ni, Co, P, Ge, Sb, In, Bi, Zn, etc. are added to these alloys can be used.

In the present invention, the flux can be prepared by heating and mixing the sorbitol-type thixotropic agent, the sorbitol-type additive and the glycol ether-type solvent through a method known in the art. By kneading this flux and the solder powder through a method known in the art, the solder paste can be produced.

The thus prepared solder paste in the present invention can be applied to a soldering part of a circuit board of microstructure in electronic equipment by, for example, a printing method using a metal mask, a discharge method using a dispenser, or a transfer method using a transfer pin, whereby reflowing can be carried out.

The present invention will be more specifically described with reference to examples, but the present invention is in no way limited to the contents described in the examples.

EXAMPLES (Evaluation)
The fluxes of Examples 1 to 46 and Comparative Examples 1 and 2 were each subjected to (1) Evaluation of precipitation of aggregate, (2) Evaluation of thixotropic ratio, and (3) Comprehensive evaluation, as below.

(1) Evaluation of Precipitation of Aggregate
(1-1) Evaluation of Flux
100 ml of each of the fluxes of Examples 1 to 46 and Comparative Examples 1 and 2 was sampled, placed in a glass beaker container having a volume of 200 ml and stirred 10 times with a dispensing spoon, thereby preparing samples for visual observation. By carrying out the same operations, three samples for visual observation were prepared for each flux, and the samples were visually observed.

(1-2) Evaluation of Solder Paste
The fluxes of Examples 1 to 46 and Comparative Examples 1 and 2 and a spherical powder (diameter 32 μm) of a solder alloy were provided, and each flux and the powder were mixed in such a manner that the amount of each of the fluxes of Examples 1 to 46 and Comparative Examples 1 and 2 and the amount of the solder alloy powder were 11 mass % and 89 mass % based on the whole solder paste, respectively, thereby obtaining solder pastes. The composition of the solder alloy used was Sn-3Ag-0.5Cu (each numerical value is in mass %).

The resulting solder pastes of Examples 1 to 46 and Comparative Examples 1 and 2 were each subjected to measurement three times using grindometer GS-2256M (manufactured by Taiyukizai Co., Ltd., measuring range: 0 to 100 μm). Then a mean value of the found values of three times was calculated, and this mean value was taken as a size (granularity) of an aggregate contained in the solder paste.

Figure 2:
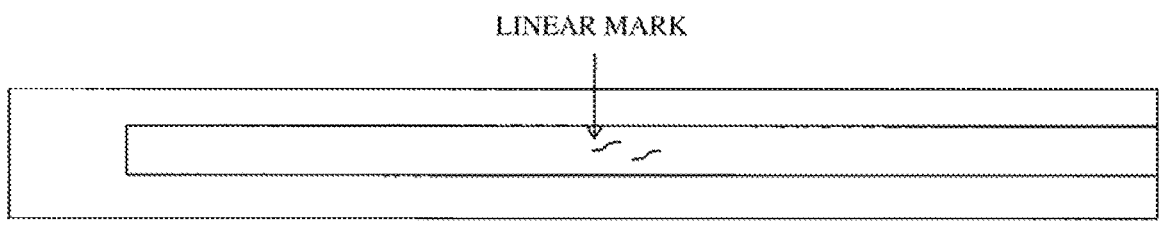
FIG. 2 is a top view showing a state of the sample measured in FIG. 1.

FIG. 1 is a schematic view showing a state of measurement of a sample using a grindometer. A surface of the grindometer is provided with a groove whose depth increases from 0 at one end to the maximum value at the other end at a constant value, and when a solder paste sample is squeezed by a scraper from the maximum depth side, linear marks or granular marks remain at the positions of depths corresponding to the sizes of aggregates (see FIG. 2). Based on the depths at the positions at which linear marks or granular marks had been formed, the sizes (granularity) of the aggregates in the solder paste sample were evaluated.

(1-3) Judgement Criteria

Regarding all the three flux samples, an aggregate is not observed, and in each of the measurement of three times for the solder paste sample, any linear mark or granular mark is not generated on the grindometer: ○○ (extremely good)

Regarding all the three flux samples, an aggregate is not observed, and in the solder paste sample, an aggregate of 50 μm or more is not observed: ○ (good)

In any one of the three flux samples, an aggregate is observed, and/or, in the solder paste sample, an aggregate of 50 μm or more is observed: x (poor)

(2) Evaluation of Thixotropic Ratio

Solder pastes of Examples 1 to 46 and Comparative Examples 1 and 2 were obtained in the same manner as in the above "(1-2) Evaluation of solder paste" of "(1) Evaluation of precipitation of aggregate".

Regarding each of the resulting solder pastes of Examples 1 to 46 and Comparative Examples 1 and 2, viscosities were sequentially measured according to the number of revolutions (rpm) and the measuring time (min) shown in the following Table 1 under the conditions of 25° C. using a double cylinder type rotational viscometer Malcom Viscometer PCU-205 (manufactured by Malcom Co., Ltd.). From the viscosities at 3 rpm and 30 rpm, a thixotropic ratio was determined based of the following formula (1).

TABLE 1

| | Number of revolutions | | | | | | | |
|---|---|---|---|---|---|---|---|---|
| | 10 | 3 | 4 | 5 | 10 | 20 | 30 | 10 |
| Measuring time | 3 | 6 | 3 | 3 | 3 | 2 | 2 | 1 |

[Formula 1]

$$\text{Thixotropic ratio} = \text{LOG}(\text{viscosity at 3 revolutions}/\text{viscosity at 30 revolutions}) \quad (1)$$

Evaluation was carried out according to the following judgement criteria.

The thixotropic ratio is 0.4 or more, and the thixotropy is sufficient: ○ (good) The thixotropic ratio is less than 0.4, and the thixotropy is insufficient: x (poor)

(3) Comprehensive Evaluation

Comprehensive evaluation was carried out according to the following judgement criteria.

(1) Evaluation of precipitation of aggregate is ○○ (extremely good), and (2) Evaluation of thixotropic ratio is ○ (good): ○○ (extremely good)

(1) Evaluation of precipitation of aggregate is ○ (good), and (2) Evaluation of thixotropic ratio is ○ (good): ○ (good)

At least one of (1) Evaluation of precipitation of aggregate and (2) Evaluation of thixotropic ratio is x (poor): x (poor)

Examples 1 to 46, Comparative Examples 1 and 2

Fluxes of Examples 1 to 46 and Comparative Examples 1 and 2 having compositions shown in the following Tables 2 to 7 were prepared.

The numerical values of the components in the following Tables 2 to 7 each are the content in mass % of the component based on the mass of the whole flux.

Regarding the fluxes of Examples 1 to 46 and Comparative Examples 1 and 2, the aforesaid (1) Evaluation of precipitation of aggregate, (2) Evaluation of thixotropic ratio, and (3) Comprehensive evaluation were carried out. The evaluation results are set forth in the following Tables 2 to 7.

[Table 2]

TABLE 2

| | | Example | | | | | | | | | |
|---|---|---|---|---|---|---|---|---|---|---|---|
| | | 1 | 2 | 3 | 4 | 5 | 6 | 7 | 8 | 9 | 10 |
| Sorbitol-type thixotropic agent | Dibenzylidene-D-sorbitol | 1.5 | 1.5 | 1.5 | 1.5 | 1.5 | 1.5 | | | | |
| | Bis(4-methylbenzylidene)-D-sorbitol | | | | | | | 1.5 | 1.5 | | |
| Sorbitol-type additive | D-Sorbitol | 0.00075 | 0.00300 | 0.01500 | 0.00075 | 0.00300 | 0.01500 | | | | |
| | Monobenzylidene-D-sorbitol | | | | | | | 0.00300 | | | |
| | Mono(4-methylbenzylidene)-D-sorbitol | | | | | | | | 0.00300 | 0.00300 | 0.00300 |
| Content of sorbitol-type additive based on total of sorbitol-type thixotropic agent and sorbitol-type additive (mass %) | | 0.05% | 0.20% | 0.99% | 0.05% | 0.20% | 0.99% | 0.20% | 0.20% | 0.20% | 0.20% |
| Thixotropic agent (other than sorbitol-type thixotropic agent) | Hydrogenated castor oil | 2.5 | 2.5 | 2.5 | 2.5 | 2.5 | 2.5 | 2.5 | 2.5 | 2.5 | 2.5 |
| | Ethylenebishydroxystearic acid amide | 2.5 | 2.5 | 2.5 | 2.5 | 2.5 | 2.5 | 2.5 | 2.5 | 2.5 | 2.5 |
| Resin-type resin | Hydrogenated rosin | 20.0 | 20.0 | 20.0 | 20.0 | 20.0 | 20.0 | 20.0 | 20.0 | 20.0 | 20.0 |
| Modified rosin | Polymerized rosin | 25.0 | 25.0 | 25.0 | 25.0 | 25.0 | 25.0 | 25.0 | 25.0 | 25.0 | 25.0 |
| Organic acid | Carboxylic acid Glutaric acid | 1.0 | 1.0 | 1.0 | 1.0 | 1.0 | 1.0 | 1.0 | 1.0 | 1.0 | 1.0 |
| Amine compound | Imidazole 2-Phenylimidazole | 1.0 | 1.0 | 1.0 | 1.0 | 1.0 | 1.0 | 1.0 | 1.0 | 1.0 | 1.0 |
| Glycol ether-type solvent | Aromatic glycol ether-type solvent Phenyl glycol | 46.49925 | 46.49700 | 46.48500 | 46.49925 | 46.49700 | 46.48500 | 46.49700 | 46.49700 | 46.49700 | 46.49700 |
| Total amount | | 100.0 | 100.0 | 100.0 | 100.0 | 100.0 | 100.0 | 100.0 | 100.0 | 100.0 | 100.0 |
| Evaluation | Precipitation of aggregate | ○ | ○○ | ○○ | ○○ | ○○ | ○○ | ○○ | ○○ | ○○ | ○○ |
| | Thixotropic ratio | ○ | ○ | ○ | ○ | ○ | ○ | ○ | ○ | ○ | ○ |
| | Comprehensive evaluation | ○○ | ○○ | ○○ | ○○ | ○○ | ○○ | ○○ | ○○ | ○○ | ○○ |

[Table 3]

TABLE 3

| | | Example | | | | | | | |
|---|---|---|---|---|---|---|---|---|---|
| | | 11 | 12 | 13 | 14 | 15 | 16 | 17 | 18 |
| Sorbitol-type thixotropic agent | Dibenzylidene-D-sorbitol | 0.5 | 0.5 | 3.5 | 3.5 | 0.5 | 0.5 | 3.5 | |
| | Bis(4-methylbenzylidene)-D-sorbitol | | | | | | | | 3.5 |
| Sorbitol-type additive | D-Sorbitol | 0.00100 | | 0.00700 | | 0.00100 | | 0.00700 | |
| | Monobenzylidene-D-sorbitol | | 0.00100 | | 0.00700 | | 0.00100 | | |
| | Mono(4-methylbenzylidene)-D-sorbitol | | | | | | | | 0.00700 |
| Content of sorbitol-type additive based on total of sorbitol-type thixotropic agent and sorbitol-type additive (mass %) | | 0.20% | 0.20% | 0.20% | 0.20% | 0.20% | 0.20% | 0.20% | 0.20% |
| Thixotropic agent (other than sorbitol-type thixotropic agent) | Hydrogenated castor oil | 2.5 | 2.5 | 2.5 | 2.5 | 2.5 | 2.5 | 2.5 | 2.5 |
| | Ethylenebishydroxystearic acid amide | 2.5 | 2.5 | 2.5 | 2.5 | 2.5 | 2.5 | 2.5 | 2.5 |
| Resin-type resin | Hydrogenated rosin | 20.0 | 20.0 | 20.0 | 20.0 | 20.0 | 20.0 | 20.0 | 20.0 |
| Modified rosin | Polymerized rosin | 25.0 | 25.0 | 25.0 | 25.0 | 25.0 | 25.0 | 25.0 | 25.0 |
| Organic acid Carboxylic acid | Glutaric acid | 1.0 | 1.0 | 1.0 | 1.0 | 1.0 | 1.0 | 1.0 | 1.0 |
| Amine compound Imidazole compound | 2-Phenylimidazole | 1.0 | 1.0 | 1.0 | 1.0 | 1.0 | 1.0 | 1.0 | 1.0 |
| Glycol ether-type solvent Aromatic-glycol ether-type solvent | Phenyl glycol | 47.49900 | 47.49900 | 44.49300 | 44.49300 | 47.49900 | 47.49900 | 44.49300 | 44.49300 |
| Total amount | | 100.0 | 100.0 | 100.0 | 100.0 | 100.0 | 100.0 | 100.0 | 100.0 |
| Evaluation | Precipitation of aggregate | ∘∘ | ∘∘ | ∘∘ | ∘∘ | ∘∘ | ∘∘ | ∘∘ | ∘∘ |
| | Thixotropic ratio | ∘ | ∘ | ∘ | ∘ | ∘ | ∘ | ∘ | ∘ |
| | Comprehensive evaluation | ∘∘ | ∘∘ | ∘∘ | ∘∘ | ∘∘ | ∘∘ | ∘∘ | ∘∘ |

[Table 4]

TABLE 4

| | | Example | | | | | | | | | |
|---|---|---|---|---|---|---|---|---|---|---|---|
| | | 19 | 20 | 21 | 22 | 23 | 24 | 25 | 26 | 27 | 28 |
| Sorbitol-type thixotropic agent | Dibenzylidene-D-sorbitol | 1.5 | 1.5 | 1.5 | 1.5 | 1.5 | 1.5 | | | | |
| | Bis(4-methylbenzylidene)-D-sorbitol | | | | | | | 1.5 | 1.5 | 1.5 | 1.5 |
| Sorbitol-type additive | D-Sorbitol | 0.00075 | 0.00300 | 0.01500 | 0.00075 | 0.00300 | 0.01500 | | | | |
| | Monobenzylidene-D-sorbitol | | | | | | | 0.00300 | 0.00300 | | |
| | Mono(4-methylbenzylidene)-D-sorbitol | | | | | | | | | 0.00300 | 0.00300 |
| Content of sorbitol-type additive based on total of sorbitol-type thixotropic agent and sorbitol-type additive (mass %) | | 0.05% | 0.20% | 0.99% | 0.05% | 0.20% | 0.99% | 0.20% | 0.20% | 0.20% | 0.20% |
| Thixotropic agent (other than sorbitol-type thixotropic agent) | Hydrogenated castor oil | 2.5 | 2.5 | 2.5 | 2.5 | 2.5 | 2.5 | 2.5 | 2.5 | 2.5 | 2.5 |
| | Ethylenebishydroxystearic acid amide | 2.5 | 2.5 | 2.5 | 2.5 | 2.5 | 2.5 | 2.5 | 2.5 | 2.5 | 2.5 |
| Resin-type resin | Modified rosin | 20.0 | 20.0 | 20.0 | 20.0 | 20.0 | 20.0 | 20.0 | 20.0 | 20.0 | 20.0 |
| | Hydrogenated rosin | 25.0 | 25.0 | 25.0 | 25.0 | 25.0 | 25.0 | 25.0 | 25.0 | 25.0 | 25.0 |
| | Polymerized rosin | 1.0 | 1.0 | 1.0 | 1.0 | 1.0 | 1.0 | 1.0 | 1.0 | 1.0 | 1.0 |
| Organic acid | Carboxylic acid Glutaric acid | | | | | | | | | | |
| Amine compound | Imidazole 2-Phenylimidazole | 1.0 | 1.0 | 1.0 | 1.0 | 1.0 | 1.0 | 1.0 | 1.0 | 1.0 | 1.0 |
| Glycol ether-type solvent | Aliphatic glycol ether-type solvent Hexyl diglycol | 46.49925 | 46.49700 | 46.48500 | 46.49925 | 46.49700 | 46.48500 | 46.49700 | 46.49700 | 46.49700 | 46.49700 |
| Total amount | | 100.0 | 100.0 | 100.0 | 100.0 | 100.0 | 100.0 | 100.0 | 100.0 | 100.0 | 100.0 |
| Evaluation | Precipitation of aggregate | ○ | ○ | ○ | ○ | ○ | ○ | ○ | ○ | ○ | ○ |
| | Thisotropic ratio | ○ | ○ | ○ | ○ | ○ | ○ | ○ | ○ | ○ | ○ |
| | Comprehensive evaluation | ○ | ○ | ○ | ○ | ○ | ○ | ○ | ○ | ○ | ○ |

[Table 5]

TABLE 5

| | | Example | | | | | | | |
|---|---|---|---|---|---|---|---|---|---|
| | | 29 | 30 | 31 | 32 | 33 | 34 | 35 | 36 |
| Sorbitol-type thixotropic agent | Dibenzylidene-D-sorbitol | 0.5 | 0.5 | 3.5 | 3.5 | | | 3.5 | 3.5 |
| | Bis(4-methylbenzylidene)-D-sorbitol | | | | | 0.5 | 0.5 | | |
| Sorbitol-type additive | D-Sorbitol | 0.00100 | | 0.00700 | | 0.00100 | | 0.00700 | |
| | Monobenzylidene-D-sorbitol | | 0.00100 | | 0.00700 | | 0.00100 | | 0.00700 |
| | Mono(4-methylbenzylidene)-D-sorbitol | | | | | | | | |
| Content of sorbitol-type additive based on total of sorbitol-type thixotropic agent and sorbitol-type additive (mass %) | | 0.20% | 0.20% | 0.20% | 0.20% | 0.20% | 0.20% | 0.20% | 0.20% |
| Thixotropic agent (other than sorbitol-type thixotropic agent) | Hydrogenated castor oil | 2.5 | 2.5 | 2.5 | 2.5 | 2.5 | 2.5 | 2.5 | 2.5 |
| | Ethylenebishydroxystearic acid amide | 2.5 | 2.5 | 2.5 | 2.5 | 2.5 | 2.5 | 2.5 | 2.5 |
| Resin-type resin | Modified rosin | 20.0 | 20.0 | 20.0 | 20.0 | 20.0 | 20.0 | 20.0 | 20.0 |
| | Hydrogenated rosin | 25.0 | 25.0 | 25.0 | 25.0 | 25.0 | 25.0 | 25.0 | 25.0 |
| | Polymerized rosin | | | | | | | | |
| Organic acid | Carboxylic acid | 1.0 | 1.0 | 1.0 | 1.0 | 1.0 | 1.0 | 1.0 | 1.0 |
| | Glutaric acid | | | | | | | | |
| Amine compound | Imidazole compound | 1.0 | 1.0 | 1.0 | 1.0 | 1.0 | 1.0 | 1.0 | 1.0 |
| | 2-Phenylimidazole | | | | | | | | |
| Glycol ether-type solvent | Aliphatic glycol ether-type solvent | 47.49900 | 47.49900 | 44.49300 | 44.49300 | 47.49900 | 47.49900 | 44.49300 | 44.49300 |
| | Hexyl diglycol | | | | | | | | |
| Total amount | | 100.0 | 100.0 | 100.0 | 100.0 | 100.0 | 100.0 | 100.0 | 100.0 |
| Evaluation | Precipitation of aggregate | ○ | ○ | ○ | ○ | ○ | ○ | ○ | ○ |
| | Thixotropic ratio | ○ | ○ | ○ | ○ | ○ | ○ | ○ | ○ |
| | Comprehensive evaluation | ○ | ○ | ○ | ○ | ○ | ○ | ○ | ○ |

[Table 6]

|  |  | Example | | | | | | | | | |
|---|---|---|---|---|---|---|---|---|---|---|---|
|  |  | 37 | 38 | 39 | 40 | 41 | 42 | 43 | 44 | 45 | 46 |
| Sorbitol-type thixotropic agent | Dibenzylidene-D-sorbitol | 1.5 | 1.5 | 1.5 | 1.5 | 1.5 | 1.5 | 1.5 | 1.5 | 1.5 | 1.5 |
| Sorbitol-type additive | D-Sorbitol | 0.00300 | 0.00300 | 0.00300 | 0.00300 | 0.00300 | 0.00300 | 0.00300 | 0.00300 | 0.00300 | 0.00300 |
| Content of sorbitol-type additive based on total of sorbitol-type thixotropic agent and sorbitol-type additive (mass %) |  | 0.20% | 0.20% | 0.20% | 0.20% | 0.20% | 0.20% | 0.20% | 0.20% | 0.20% | 0.20% |
| Thixotropic agent (other than sorbitol-type thixotropic agent) | Hydrogenated castor oil | 5.0 | 5.0 | 5.0 | 2.5 | 2.5 | 2.5 | 2.5 | 2.5 | 2.5 | 2.5 |
|  | Ethylenebishydroxystearic acid amide | 5.0 | 5.0 | 5.0 | 2.5 | 2.5 | 2.5 | 2.5 | 2.5 | 2.5 | 2.5 |
| Resin-type resin | Natural resin | Natural resin |  |  | 10.0 |  |  |  |  |  |  |
|  | Modified rosin | Hydrogenated rosin | 20.0 | 20.0 |  | 30.0 | 20.0 | 20.0 | 20.0 | 20.0 | 20.0 | 20.0 |
|  |  | Polymerized rosin | 25.0 | 25.0 |  |  | 25.0 | 25.0 | 25.0 | 25.0 | 25.0 | 25.0 |
|  |  | Disproportionated rosin |  |  | 10.0 |  |  |  |  |  |  |  |
|  |  | Acid-modified rosin |  |  |  | 20.0 |  |  |  |  |  |  |
|  |  | Rosin ester |  |  |  | 10.0 |  |  |  |  |  |  |
| Organic acid | Carboxylic acid | Glutaric acid | 1.0 | 1.0 | 1.0 | 1.0 | 1.0 | 1.0 | 1.0 | 1.0 | 1.0 | 1.0 |
|  |  | Sebacic acid |  |  |  |  |  |  |  |  |  |  |
| Amine compound | Imidazole | 2-Phenylimidazole | 1.0 | 1.0 | 1.0 |  | 1.0 | 1.0 | 1.0 | 1.0 | 1.0 | 1.0 |
| Halogen compound | Organohalogen compound | trans-2,3-Dibromo-2-butene-1,4-diol |  |  |  |  |  |  |  |  |  |  |
|  |  | Triallyl isocyanurate hexabromide |  |  |  |  | 5.0 | 5.0 |  |  |  |  |
|  | Amine hydrohalide salt | Monoethylamine hydrobromide |  |  |  |  |  |  | 3.0 |  |  |  |
| Antioxidant | 2,2'-Methylenebis[6-(1-methylzyclohexyl)-p-cresol] |  |  |  |  |  |  |  |  |  |  | 2.0 |
| Glycol ether-type solvent | Aromatic-glycol ether-type solvent | Phenyl glycol | 50.49700 | 41.49700 | 66.49700 | 31.49700 | 42.49700 | 42.49700 | 44.49700 | 37.49700 | 46.49700 | 41.49700 |
| Total amount |  |  | 100.0 | 100.0 | 100.0 | 100.0 | 100.0 | 100.0 | 100.0 | 100.0 | 100.0 | 100.0 |
| Evaluation | Precipitation of aggregate |  | ○○ | ○○ | ○○ | ○○ | ○○ | ○○ | ○○ | ○○ | ○○ | ○○ |
|  | Thisotropic ratio |  | ○ | ○ | ○ | ○ | ○ | ○ | ○ | ○ | ○ | ○ |
|  | Comprehensive evaluation |  | ○○ | ○○ | ○○ | ○○ | ○○ | ○○ | ○○ | ○○ | ○○ | ○○ |

[Table 7]

TABLE 7

|  |  | Comparative Example | |
|---|---|---|---|
|  |  | 1 | 2 |
| Sorbitol-type thixotropic agent | Dibenzylidene-D-sorbitol | 3.0 | 0.1 |
| Sorbitol-type additive | D-Sorbitol |  | 0.00300 |
| Content of sorbitol-type additive based on total of sorbitol-type thixotropic agent and sorbitol-type additive (mass %) |  | 0.00% | 2.91% |
| Thixotropic agent (other than sorbitol-type thixotropic agent) | Hydrogenated castor oil | 2.5 | 0.5 |
|  | Ethylenebis-hydroxystearic acid amide | 2.5 | 0.5 |
| Rosin-type resin | Modified rosin | Hydrogenated rosin | 20.0 | 20.0 |
|  |  | Polymerized rosin | 25.0 | 25.0 |
| Organic acid | Carboxylic acid | Glutaric acid | 1.0 | 1.0 |
| Amine compound | Imidazole compound | 2-Phenyl-imidazole | 1.0 | 1.0 |
| Glycol ether-type solvent | Aliphatic glycol ether-type solvent | Hexyl diglycol | 45.00000 |  |
|  | Aromatic glycol ether-type solvent | Phenyl glycol |  | 51.89700 |
|  | Total amount |  | 100.0 | 100.0 |
| Evaluation | Precipitation of aggregate |  | x | ○○ |
|  | Thixotropic ratio |  | ○ | x |
|  | Comprehensive evaluation |  | x | x |

According to the results of the above Tables 2 and 3, regarding the fluxes of Examples 1 to 18 each containing 0.5 to 3.5 mass % of a sorbitol-type thixotropic agent selected from dibenzylidene sorbitol and bis(4-methylbenzylidene) sorbitol and 2 to 350 mass ppm (0.0002 to 0.035 mass %) of a sorbitol-type additive selected from sorbitol, monobenzylidene sorbitol and mono(4-methylbenzylidene)sorbitol and phenyl glycol, which is an aromatic glycol ether-type solvent, as a solvent, precipitation of aggregates was not observed in both states of a flux and a solder paste, resulting in extremely good ratings, and the solder pastes each had a thixotropic ratio of 0.4 or more and thus had sufficient thixotropy.

As can be seen from the results of Examples 1 to 18, even though the type and the content (mass %) of each of the sorbitol-type thixotropic agent and the sorbitol-type additive were changed, there was no change in both evaluation of the precipitation of aggregate and the thixotropic ratio, resulting in extremely good or good ratings.

According to the results of the above Tables 4 and 5, regarding the fluxes of Examples 19 to 36 each containing 0.5 to 3.5 mass % of a sorbitol-type thixotropic agent selected from dibenzylidene sorbitol and bis(4-methylbenzylidene)sorbitol and 2 to 350 mass ppm (0.0002 to 0.035 mass %) of a sorbitol-type additive selected from sorbitol, monobenzylidene sorbitol and mono(4-methylbenzylidene) sorbitol and hexyl diglycol, which is an aliphatic glycol ether-type solvent, as a solvent, precipitation of aggregates was not observed in a state of a flux and an aggregate of 50 μm or more not observed in a state of a solder paste, resulting in good ratings. Regarding the fluxes of Examples 19 to 36, the solder pastes each had a thixotropic ratio of 0.4 or more and thus had sufficient thixotropy.

As can be seen from the results of Examples 19 to 36, even though the type and the content (mass %) of each of the sorbitol-type thixotropic agent and the sorbitol-type additive were changed, there was no change in both evaluation of the precipitation of aggregate and the thixotropic ratio, resulting in good ratings.

As can be seen from comparison between the results of Examples 1 to 18 and the results of Examples 19 to 36, the effect of suppressing precipitation of aggregates in the case where phenyl glycol, which is an aromatic glycol ether-type solvent, was used as a solvent was higher than that in the case where hexyl diglycol, which is an aliphatic glycol ether-type solvent, was used.

According to the results of the above Table 6, regarding the fluxes of Examples 37 to 46 each containing 0.5 to 3.5 mass % of dibenzylidene sorbitol and 2 to 350 mass ppm (0.0002 to 0.035 mass %) of sorbitol and phenyl glycol, which is an aromatic glycol ether-type solvent, as a solvent, precipitation of aggregates was not observed in both states of a flux and a solder paste, resulting in extremely good ratings, and the solder pastes each had a thixotropic ratio of 0.4 or more and thus had sufficient thixotropy.

As can be seen from the results of Examples 37 to 46, even in the case where the contents (mass %) and/or the types of the thixotropic agent other than the sorbitol-type thixotropic agent, the rosin-type resin, the organic acid, the halogen compound and the antioxidant were changed, there was no change in both evaluation of the precipitation of aggregate and the thixotropic ratio, resulting in extremely good or good ratings.

On the other hand, according to the results of the above Table 7, regarding the flux of Comparative Example 1 containing 3.0 mass % of dibenzylidene sorbitol and not containing a sorbitol-type additive, the thixotropic ratio of the solder paste was 0.4 or more, but precipitation of aggregates was observed in a state of a flux and/or a solder paste. Regarding the flux of Comparative Example 2 having a dibenzylidene sorbitol content of 0.1 mass % and containing 300 mass ppm (0.0300 mass %) of sorbitol, precipitation of aggregates was not observed in both states of a flux and a solder paste because the content of the thixotropic agent was small, and the solder paste had a thixotropic ratio of less than 0.4 and thus had insufficient thixotropy.

As shown in Tables 2 to 7 above, it has been confirmed that a flux containing 0.5 to 3.5 mass % of a sorbitol-type thixotropic agent selected from the group consisting of dibenzylidene sorbitol, bis(4-methylbenzylidene)sorbitol and a combination thereof, and 2 to 350 mass ppm of a sorbitol-type additive selected from the group consisting of sorbitol, monobenzylidene sorbitol, mono(4-methylbenzylidene)sorbitol and a combination thereof, and a glycol ether-type solvent has high thixotropy and is suppressed in precipitation of aggregates.

The invention claimed is:

1. A flux comprising:
   0.5 to 3.5 mass % of a sorbitol-type thixotropic agent selected from the group consisting of dibenzylidene sorbitol, bis(4-methylbenzylidene)sorbitol and a combination thereof;
   2 to 350 mass ppm of a sorbitol-type additive selected from the group consisting of sorbitol, monobenzylidene sorbitol, mono(4-methylbenzylidene)sorbitol and a combination thereof; and
   a glycol ether-type solvent.

2. The flux according to claim 1, wherein a content of the sorbitol-type additive is 0.05 to 1.00 mass % based on the total amount of the sorbitol-type thixotropic agent and the sorbitol-type additive.

3. The flux according to claim 1, further comprising 1.0 to 10.0 mass % of a thixotropic agent other than the sorbitol-type thixotropic agent.

4. The flux according to claim 1, further comprising 20.0 to 60.0 mass % of a rosin-type resin and/or a water-soluble resin, 0 to 10.0 mass % of an organic acid, 0 to 5.0 mass % of an amine compound, 0 to 5.0 mass % of an organohalogen compound, 0 to 3.0 mass % of an amine hydrohalide salt, and 0 to 5.0 mass % of an antioxidant.

5. A solder paste comprising a flux and a solder powder, wherein the flux comprises:
   0.5 to 3.5 mass % of a sorbitol-type thixotropic agent selected from the group consisting of dibenzylidene sorbitol, bis(4-methylbenzylidene)sorbitol and a combination thereof;
   2 to 350 mass ppm of a sorbitol-type additive selected from the group consisting of sorbitol, monobenzylidene sorbitol, mono(4-methylbenzylidene)sorbitol and a combination thereof; and
   a glycol ether-type solvent.

6. The flux according to claim 2, further comprising 1.0 to 10.0 mass % of a thixotropic agent other than the sorbitol-type thixotropic agent.

7. The flux according to claim 2, further comprising 20.0 to 60.0 mass % of a rosin-type resin and/or a water-soluble resin, 0 to 10.0 mass % of an organic acid, 0 to 5.0 mass % of an amine compound, 0 to 5.0 mass % of an organohalogen compound, 0 to 3.0 mass % of an amine hydrohalide salt, and 0 to 5.0 mass % of an antioxidant.

8. The flux according to claim 1, further comprising 1.0 to 10.0 mass % of a thixotropic agent other than the sorbitol-type thixotropic agent, 20.0 to 60.0 mass % of a rosin-type resin and/or a water-soluble resin, 0 to 10.0 mass % of an organic acid, 0 to 5.0 mass % of an amine compound, 0 to 5.0 mass % of an organohalogen compound, 0 to 3.0 mass % of an amine hydrohalide salt, and 0 to 5.0 mass % of an antioxidant.

9. The flux according to claim 2, further comprising 1.0 to 10.0 mass % of a thixotropic agent other than the sorbitol-type thixotropic agent, 20.0 to 60.0 mass % of a rosin-type resin and/or a water-soluble resin, 0 to 10.0 mass % of an organic acid, 0 to 5.0 mass % of an amine compound, 0 to 5.0 mass % of an organohalogen compound, 0 to 3.0 mass % of an amine hydrohalide salt, and 0 to 5.0 mass % of an antioxidant.

10. The solder paste according to claim 5, wherein a content of the sorbitol-type additive is 0.05 to 1.00 mass % based on the total amount of the sorbitol-type thixotropic agent and the sorbitol-type additive.

11. The solder paste according to claim 5, wherein the flux further comprises 1.0 to 10.0 mass % of a thixotropic agent other than the sorbitol-type thixotropic agent.

12. The solder paste according to claim 5, wherein a content of the sorbitol-type additive is 0.05 to 1.00 mass % based on the total amount of the sorbitol-type thixotropic agent and the sorbitol-type additive, and wherein the flux further comprises 1.0 to 10.0 mass % of a thixotropic agent other than the sorbitol-type thixotropic agent.

13. The solder paste according to claim 5, wherein the flux further comprises 20.0 to 60.0 mass % of a rosin-type resin and/or a water-soluble resin, 0 to 10.0 mass % of an organic acid, 0 to 5.0 mass % of an amine compound, 0 to 5.0 mass % of an organohalogen compound, 0 to 3.0 mass % of an amine hydrohalide salt, and 0 to 5.0 mass % of an antioxidant.

14. The solder paste according to claim 5, wherein a content of the sorbitol-type additive is 0.05 to 1.00 mass % based on the total amount of the sorbitol-type thixotropic agent and the sorbitol-type additive, and wherein the flux further comprises 20.0 to 60.0 mass % of a rosin-type resin and/or a water-soluble resin, 0 to 10.0 mass % of an organic acid, 0 to 5.0 mass % of an amine compound, 0 to 5.0 mass % of an organohalogen compound, 0 to 3.0 mass % of an amine hydrohalide salt, and 0 to 5.0 mass % of an antioxidant.

15. The solder paste according to claim 5, wherein the flux further comprises 1.0 to 10.0 mass % of a thixotropic agent other than the sorbitol-type thixotropic agent, 20.0 to 60.0 mass % of a rosin-type resin and/or a water-soluble resin, 0 to 10.0 mass % of an organic acid, 0 to 5.0 mass % of an amine compound, 0 to 5.0 mass % of an organohalogen compound, 0 to 3.0 mass % of an amine hydrohalide salt, and 0 to 5.0 mass % of an antioxidant.

16. The solder paste according to claim 5, wherein a content of the sorbitol-type additive is 0.05 to 1.00 mass % based on the total amount of the sorbitol-type thixotropic agent and the sorbitol-type additive, and wherein the flux further comprises 1.0 to 10.0 mass % of a thixotropic agent other than the sorbitol-type thixotropic agent, 20.0 to 60.0 mass % of a rosin-type resin and/or a water-soluble resin, 0 to 10.0 mass % of an organic acid, 0 to 5.0 mass % of an amine compound, 0 to 5.0 mass % of an organohalogen compound, 0 to 3.0 mass % of an amine hydrohalide salt, and 0 to 5.0 mass % of an antioxidant.

\* \* \* \* \*